(12) United States Patent
Shih

(10) Patent No.: US 8,366,273 B2
(45) Date of Patent: Feb. 5, 2013

(54) IRIS IMAGE DEFINITION ESTIMATION SYSTEM USING THE ASTIGMATISM OF THE CORNEAL REFLECTION OF A NON-COAXIAL LIGHT SOURCE

(75) Inventor: Sheng-Wen Shih, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 114 days.

(21) Appl. No.: 13/018,116

(22) Filed: Jan. 31, 2011

(65) Prior Publication Data
US 2012/0194784 A1 Aug. 2, 2012

(51) Int. Cl.
*A61B 3/10* (2006.01)
(52) U.S. Cl. ........................................ 351/221; 351/212
(58) Field of Classification Search ........... 351/200–246
See application file for complete search history.

(56) References Cited

U.S. PATENT DOCUMENTS

| | | | |
|---|---|---|---|
| 6,252,977 B1 * | 6/2001 | Salganicoff et al. | 382/117 |
| 6,687,389 B2 * | 2/2004 | McCartney et al. | 382/118 |
| 7,418,115 B2 * | 8/2008 | Northcott et al. | 382/117 |
| 2002/0051116 A1 * | 5/2002 | Van Saarloos et al. | 351/204 |

* cited by examiner

*Primary Examiner* — Mohammed Hasan
(74) *Attorney, Agent, or Firm* — Muncy, Geissler, Olds & Lowe, PLLC

(57) ABSTRACT

An iris image definition estimation system using the astigmatism of the corneal reflection of a non-coaxial light source to assess both the resolution of the iris patterns and the direction of focus adjustment. The corneal reflection results in two virtual images on the meridional and the sagittal planes. These virtual images are formed behind the cornea and close to the iris. Yet, both are projected onto the same location and result in a composite glint area. In addition, the shape of the glint area of a non-coaxial light source varies with different camera focus settings. Furthermore, due to the high intensity of the glint area, the shape can be easily observed, and the size and the shape of the glint area can be used to determine the resolution of the iris image and the direction of focus adjustment, respectively.

8 Claims, 6 Drawing Sheets

IRIS IMAGE DEFINITION ESTIMATION SYSTEM USING THE ASTIGMATISM OF THE CORNEAL REFLECTION OF A NON-COAXIAL LIGHT SOURCE

BACKGROUND OF THE INVENTION

1. Field of the Invention

The present invention relates to an iris image definition estimation system using the astigmatism of the corneal reflection of a non-coaxial light source. More specifically, the present invention relates to a system using the astigmatism of the corneal reflection of a non-coaxial source to produce two virtual images of the light source on the meridional and sagittal image planes, and utilizes the shape of the composite virtual images to determine the resolution of an iris image and the direction of focus adjustment.

2. Description of the Prior Art

The iris is a complex structure in the eye and is a fibrous membrane consisting of an anterior layer of stroma and a posterior layer of epithelia cells. In general, the stroma layer has many unique features (e.g. crypts, collaret, and pupillary ruffs, etc.) around the pupil. The unique nature of the iris results in a set of binary features with more than 240 degrees of freedom which is notably higher than 80 degrees of freedom of the face and 20 to 40 degrees of freedom of fingerprints. Due to the fine texture of the iris, the probability of having the same iris texture is around 1 in 10 to the $78^{th}$ power. Consequently, the patterns of the left and right iris of an individual may vary significantly. In addition, an iris pattern will not change as one ages. Thus far, iris recognition has achieved the highest recognition accuracy among all the commercialized biometric technologies and it is almost impossible to forge an iris pattern. The human iris is a tiny structure with a diameter around 1 cm. Hence, to obtain a high resolution iris pattern at a comfortable distance, a telephoto lens with a long focal length is necessary. However, the depth of the field of a telephoto lens is very shallow, and, therefore, only cameras with auto-focusing or guided focusing mechanism can produce a high resolution image for iris recognition. Both auto-focusing and guided focusing require a determination of the following factors: (a) a focus measure representing the resolution of the image and (b) the direction of the focus adjustment. In general, the focus measure of the image was determined by measurement of the intensity of the image high frequency components. Due to the extensive workload, a real-time calculation of the resolution cannot easily be achieved. Though Park and Kim used a near coaxial light source to significantly reduce the time for calculation, their method of iris focusing estimation technology cannot provide a focus adjustment direction from a single image when the iris pattern is close to the focus distance. Therefore, excess time has to be wasted in exploring the direction of focusing. Moreover, the unpredictable head movements of a user also contributes to multiple errors during the process of auto focus and can dramatically increase the time required for image acquisition.

A typical example for guided focusing iris imaging system is presented in U.S. Pat. No. 5,291,560A, example 1. This system is equipped with a camera, a semi-mirror and a small monitor. The semi-mirror is used to align the camera and the monitor. Images captured by the camera are shown on the monitor which provides feedback to aid the users in alignment and position adjustment of their heads so as to enhance the resolution of the iris pattern. Meanwhile, an image processing unit can automatically determine if the resolution of the iris image is acceptable for iris recognition. During the process, no assistance is available, thus, personnel training is necessary for image acquisition. Once the resolution of an image is qualified, the image undergoes a series of processes: iris localization, unwrapping, and feature extraction. Finally, the extracted feature is compared with the feature database for accurate identification.

Another system, US 2004/0101170A1 (example 2), utilizes the intensity of the high frequency signal to determine the resolution of the iris image. First, the system determines whether the outer boundary of the upper and lower eyelids can be found in the image or not. If the boundary is faint, then the image will be classified as blurry. Images passing the initial screening will be used for simple iris localization, and an region of interest (ROI) of the iris area around the pupil will be extracted. The sides of the iris have less interference by the eyelids and the eyelash, therefore, the gradient intensity of the image from this area can be used to estimate the resolution of the iris pattern. Nonetheless, the gradient intensity of the iris patterns varies from person to person, and as a result, no universal standards are available for a determination of whether the resolution of the iris pattern is qualified.

Another common system used to determine the resolution of an iris image by depth measurement is U.S. Pat. No. 6,714,665B1, example 3, which utilizes a pair of wide angle cameras to locate 3-D locations of the users' head and eye and to adjust the orientation of a flat mirror so as to allow another camera with a telephoto lens to capture the iris pattern of one of the user's eyes. During the eye-searching process of the controlling reflective mirror, the corneal reflection of two light sources was used to confirm the location of the eye. This system requires preliminary calibration and three cameras to locate the eye. The detailed information was obtained after calculation of the distance from the focus of the camera to the eye. In the process of tuning for sharp focus, a trial and error method was used. First, adjust the focus towards one direction, if the image is faint, re-adjust the focus towards the other direction, and vice versa. Such adjustments produce a sharp image. Nevertheless, this system is not cost-effective and is difficult to calibrate. Moreover, during the process of auto focus, slight movement of the user's head will significantly affect the time for adjustment and result in multiple errors.

An additional example is a portable iris recognition system using the intensity of the high frequency signal to determine the resolution of an iris image in U.S. Pat. No. 6,753,919B1 (example 4). For the purpose of auto focus, a concave cold mirror which reflects the visible lights while allowing the infrared light to pass is placed in front of the camera. The users can see the enlarged image of their eyes through the reflection of the concave mirror and the infrared image of the iris pattern is acquired by the camera. The image resolution is calculated after processing the image through a high-pass filter for evaluating the intensity of the high frequency components. An additional mirror can be added to this system and allows the users to see images of their eyes easily. However, this system is not equipped with a guided focusing system. Thus, the users have to speculate the distance in order to obtain a sharp image.

One example for determination of the resolution of the iris image is described in U.S. Pat. No. 7,095,901B2 (example 5). Extra lighting is added to the iris image acquisition system so as to accurately locate the position of a user's forehead and cheek for focusing calculation. This patent provides two possible methods: one is to estimate the distance using an extra camera, and the other is switching the iris photographing camera between two modes, distance measurement and image acquisition. The major problem of this method is that the distances between the camera and the user's head, and the iris pattern are not the same. Hence, the depth information of the forehead and/or the cheek cannot assure the resolution of an iris pattern.

Finally, a system using a near coaxial light to estimate the resolution of the iris image was reported by Park and Kim earlier (Kang Ryoung Park and Jaihie Kim, "A Real-Time Focusing Algorithm for Iris Recognition Camera", IEEE Transactions on Systems, Man, and Cybernetics, Vol. 35, No. 3, pp. 441-444, August 2005 (example 6). This system utilizes coaxial light as the incident light source, and the coaxial light will form a virtual image behind the cornea and near the iris after corneal reflection. If the focus of the camera is inaccurate, this virtual image will form a large glint area in a round shape due to defocus. Therefore, the size of the glint area can provide information of whether the iris image has high resolution or not. Since the intensity of the glint is inversely proportional to the distance between the eye and the camera, when the eye is away from the focused distance of the camera, the intensity of the glint can be used to discriminate the direction of focus adjustment. However, when the iris pattern is close to the focus distance, the techniques mentioned in example 6 can only estimate the resolution of an image, not the direction of focus adjustment. Accordingly, a trial-and-error method is also necessary for auto focus, and as mentioned above, slight movements of the user's head will significantly affect the time for adjustment and result in multiple errors.

SUMMARY OF THE INVENTION

The present invention features an iris image definition estimation system using the astigmatism of the corneal reflection of a non-coaxial light source. With the aid of a non-coaxial light source, a single image can be used to determine both the resolution of an image and the direction of focus adjustment. The said system can not only simplify the calculation required for obtaining a high-definition iris image at a video rate, but can also be used in iris auto focus or guided focus adjustment.

In one aspect, the invention also provides a novel iris image definition estimation system using the astigmatism of the corneal reflection of a non-coaxial light source. The non-coaxial light source produces an incident light which transmitted into the cornea at an oblique angle deviating from the optical axis of the camera and the focus displacement value is measured using the astigmatic effect of the corneal reflection. By changing the focused distance of the camera lens, the camera records the corneal reflection of the non-coaxial light source known as the glint area. The shape of the glint area will change according to different focus settings. The major characteristic is to utilize the shape of the glint area for an estimation of the resolution of the iris image and the direction of focusing adjustment.

The iris image definition estimation system using the astigmatism of the corneal reflection of a non-coaxial light source consists of the following components:

A non-coaxial light source is used to produce an incident light, and the incident light deviating from the optical axis is transmitted into the cornea at an oblique angle. A meridional virtual image and a sagittal virtual image are then formed behind the cornea due to astigmatism. For example, if the light is placed directly below the camera, the meridional plane of the optical system will be the vertical plane, while the sagittal plane will be the horizontal plane.

An image sensor records the meridional and the sagittal images. The virtual images on the meridional and the sagittal planes are located at different focal planes which form a composite glint area on the image plane and provide information to the direction for focusing adjustment. If the image sensor is focused at a distance near the meridional virtual image, the meridional virtual image is clearly imaged while the sagittal virtual image is defocused and vice versa. Both the two virtual images are projected onto the same location on the image sensor and form a composite glint area.

An image processing module extracts the shape information of the composite glint area. The size of the composite glint area can be used to determine the resolution of the image and the shape of the glint area can provide information for focus adjustment.

BRIEF DESCRIPTION OF THE DRAWINGS

The drawings disclose an illustrative embodiment of the present invention which serves to exemplify the various advantages and objects hereof, and are described as follows.

DETAILED DESCRIPTION OF THE PREFERRED EMBODIMENT

Figure 1:
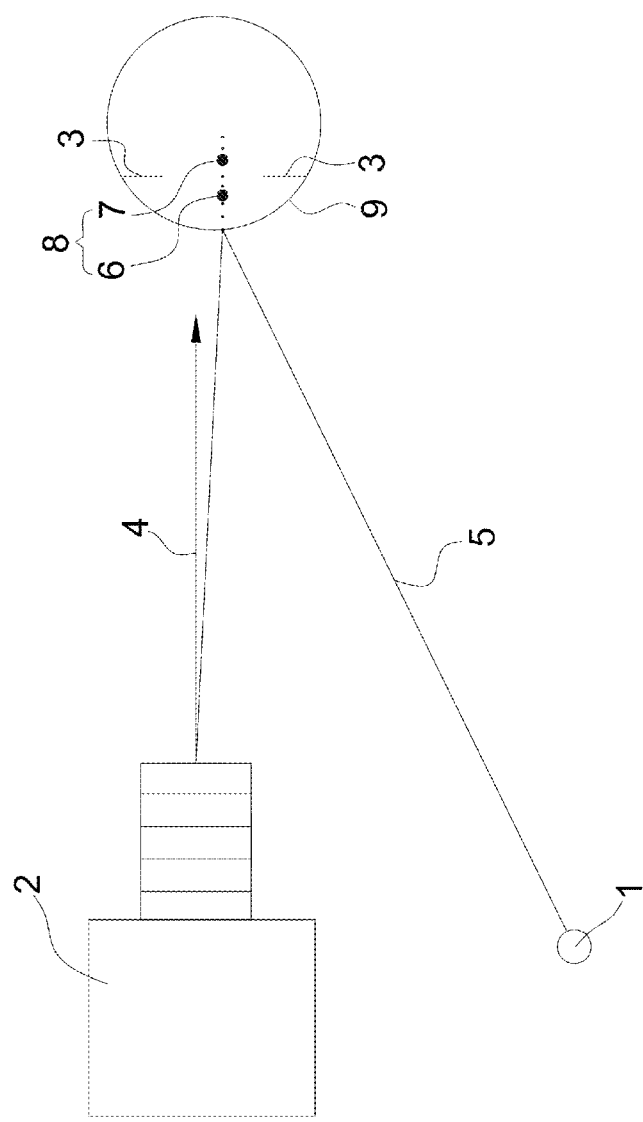
FIG. 1 is a schematic diagram of the iris image definition estimation system using the astigmatism of the corneal reflection of a non-coaxial light source according to an embodiment of the present invention.
Figure 2A:
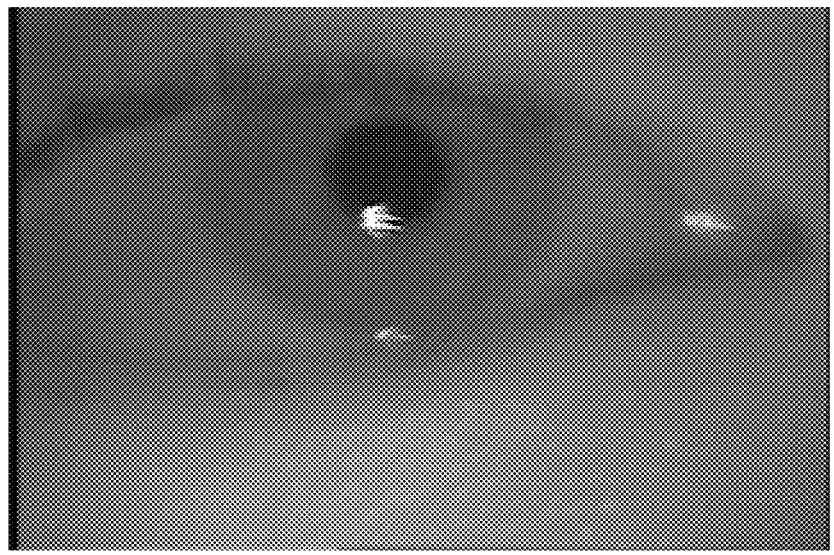
FIG. 2a to FIG. 2e shows the variation of the composite glint area of sequential iris images captured at different focus settings using the iris image definition estimation system. The composite glint area is the recorded corneal reflection of a non-coaxial light source.
Figure 2B:
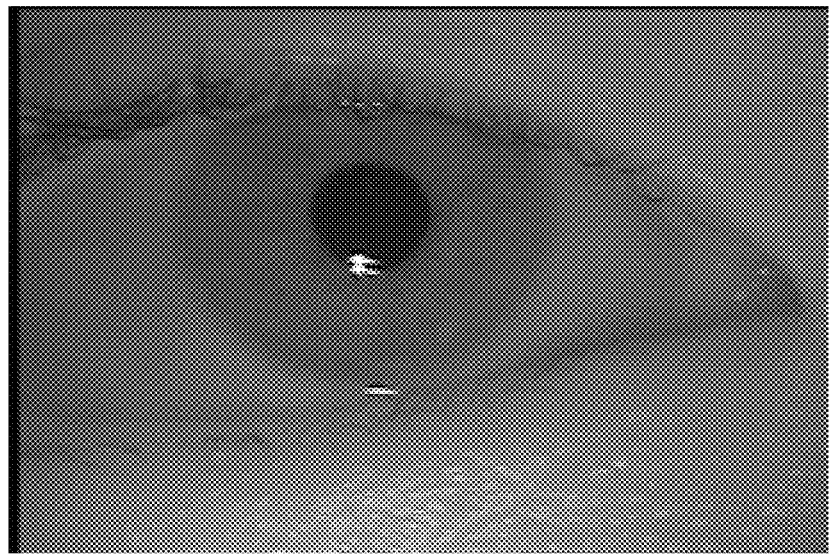
Figure 2C:
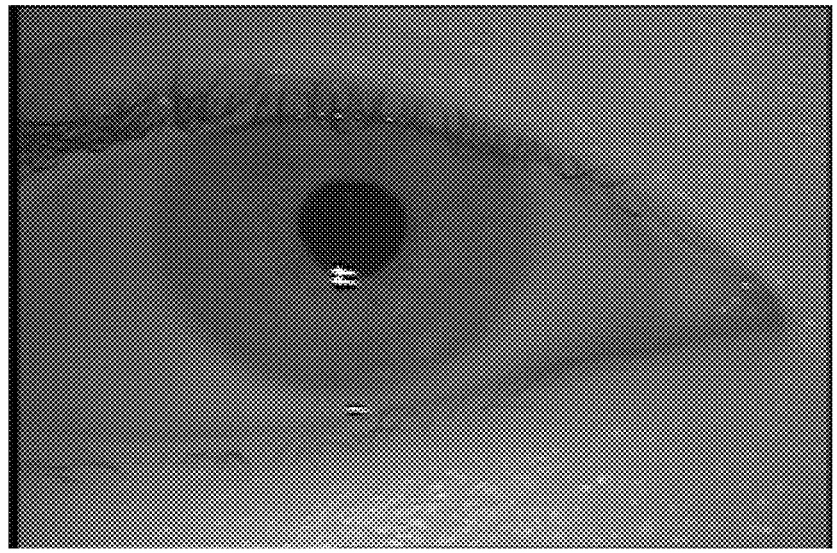
Figure 2D:
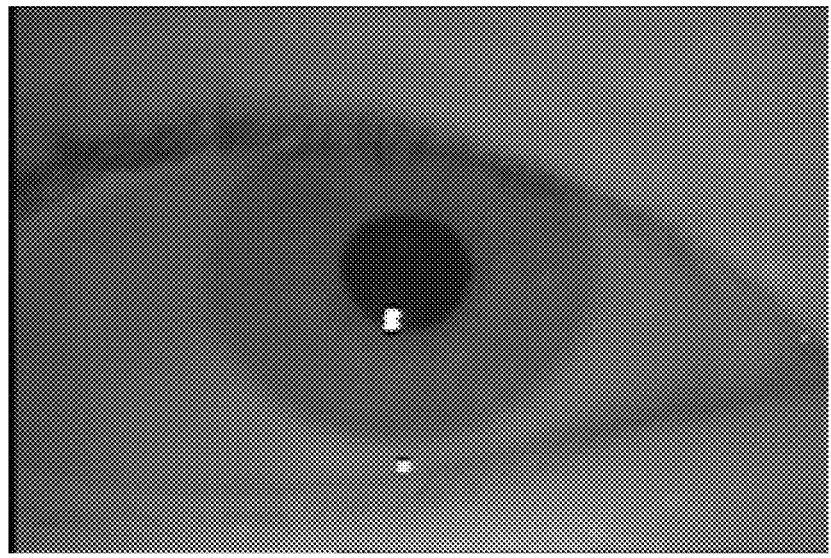
Figure 2E:
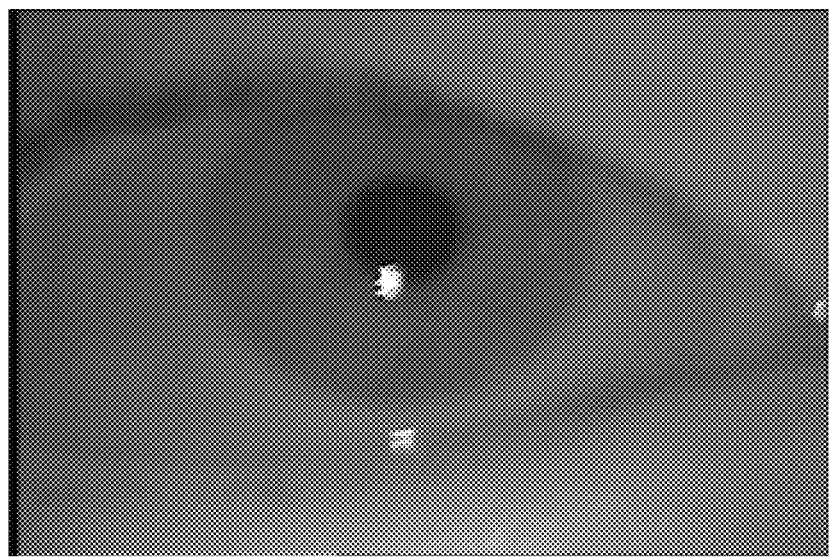

As shown in FIG. 1, the present invention provides an iris image definition estimation system using astigmatism of the corneal reflection of a non-coaxial light source which further comprises a non-coaxial light source 1, which is used to produce an incident light 5. Incident light 5 is transmitted into cornea 9 at an oblique angle deviating from the optical axis 4. The meridional virtual image 6 and the sagittal virtual image 7 are then formed behind the cornea due to astigmatism of the corneal reflection. An image sensor 2 records the composite glint area formed by both the meridional virtual image 6 and the sagittal virtual image 7, and subsequently provides the information for adjustment of the focus setting. If the sensor 2 focuses at a distance near the meridional virtual image 6, the glint area spreads narrowly along the meridional direction because it is clearly focused. On the other hand, if the sensor 2 focuses at a distance near the sagittal virtual image 7, the glint area spreads narrowly along the sagittal direction.

Focusing towards the location of either the sagittal or meridional virtual images results in different shapes of the composite glint area of image points 8. In addition, the size of the area of the composite glint can be used to estimate the focusing accuracy, while the shape of the composite glint can be used to estimate the direction of focusing.

As shown in FIG. 1, non-coaxial light source 1 is the primary light source, and the number of non-coaxial light sources 1 is unlimited. When the non-coaxial light source 1 produces an incident light 5 which is transmitted into cornea 9 at an oblique angle deviating from the axis 4, the astigmatism causes the formation of the un-reciprocal meridional virtual image 6 and sagittal virtual image 7 behind the cornea. Astigmatism is an imperfect reflection property of the cornea which yields two virtual images of the original light source behind the cornea and these two virtual images are located at two different locations which cannot be clearly focused simultaneously. Ideally, if the image sensor is focused at one of the virtual images, then the focused virtual image shrinks to a sharp point, but the other virtual image would disperse. Since the directions of dispersion of the two virtual images are perpendicular, the shape of the resulting composite glint area will vary with the change of focus setting.

When the distance between the non-coaxial light source 1 and the eye is longer than the corneal curvature radius, the subtle change of the eye location to these two images can be ignored. The following description is the method of estimation of the level of focusing and focusing direction: If the focus of the sensor 2 is adjusted from one side of the meridional virtual image 6 (as shown in FIG. 1, shorter distance) to the sagittal virtual image 7 (as shown in FIG. 1, longer distance), the sequential images captured are shown in FIG. 2a to FIG. 2e (in this example, two non-coaxial light sources were placed below the sensor, therefore, the meridional surface is vertical and the sagittal surface is horizontal. Two light sources were used, hence, two reflective points.)

Figure 3:
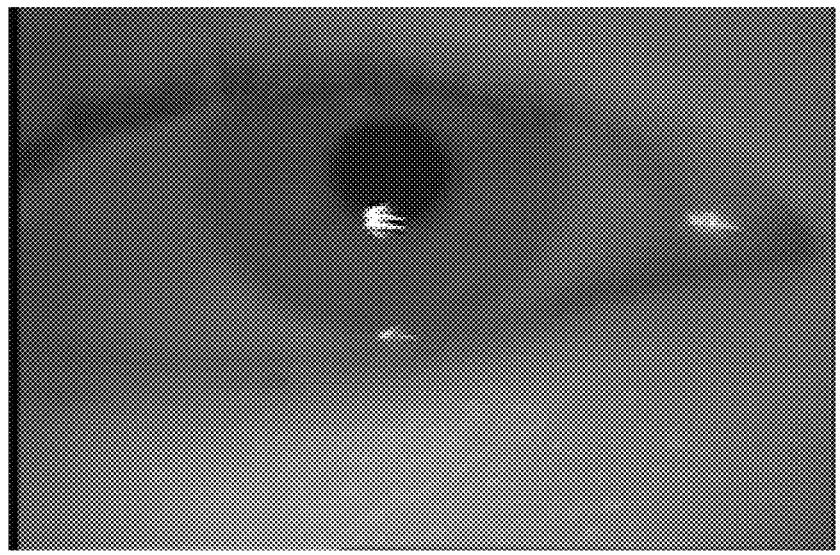
FIG. 3 is an iris image captured by the iris image definition estimation system where the camera focused at the meridonal virtual image and, thus, the meridonal virtual image is clearly focused whereas the sagittal virtual image is defocused. Since the non-coaxial light source is located below the camera, the meridonal plane and the sagittal plane are the vertical and the horizontal planes, respectively. Therefore, a defocused sagittal virtual image yields a composite glint area spreading widely in the horizontal direction.
Figure 4:
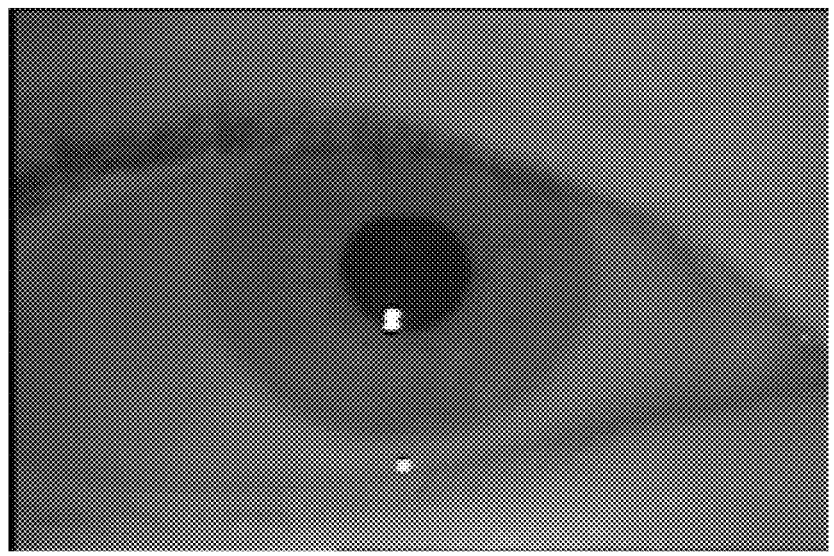
FIG. 4 is an iris image captured by the iris image definition estimation system where the camera focused at the sagittal virtual image and, thus, the sagittal virtual image is clearly focused whereas the meridonal virtual image is defocused. The resulting composite glint area will be stretched high in the vertical direction.

As shown in FIG. 3, since the focus was adjusted near the meridional virtual image 6, the virtual image on the meridional (vertical) plane is clearly focused and the virtual image on the sagittal (horizontal) plane become blurry and the glint area disperses along the sagittal (horizontal) direction. Similarly, in FIG. 4, the focus was adjusted near the sagittal virtual image 7, and consequently, the virtual image on the sagittal plane is clearly focused and the glint area dispersed along the meridional (vertical) direction. The size of the glint area of a single image can be used for estimation of the resolution of the iris 3 image, and the shape of this glint area can provide information for adjustment of focusing direction. The information intercepted by the sensor 2 can be used for auto focus or guided focus.

The image produced by corneal reflection of the non-coaxial light source 1 will be transformed by the sensor 2 into a brighter glint area and this area is distorted due to astigmatism. The sensor 2 focusing at different distances will result in different shapes of the glint area. The iris 3 is located near the image points 8 in cornea, thus, the variation of the shape of the glint area can be used to estimate the resolution of the iris 3 patterns. If the iris 3 pattern is faint, the shape of the glint area can be further used for adjustment of the focusing direction. Using the infrared light and the sensor 2, which are prerequisite for the iris 3 image acquisitions, the system can quickly estimate the resolution of the iris 3 patterns and acquire the information for adjusting the focusing direction without additional equipment.

Figure 5:
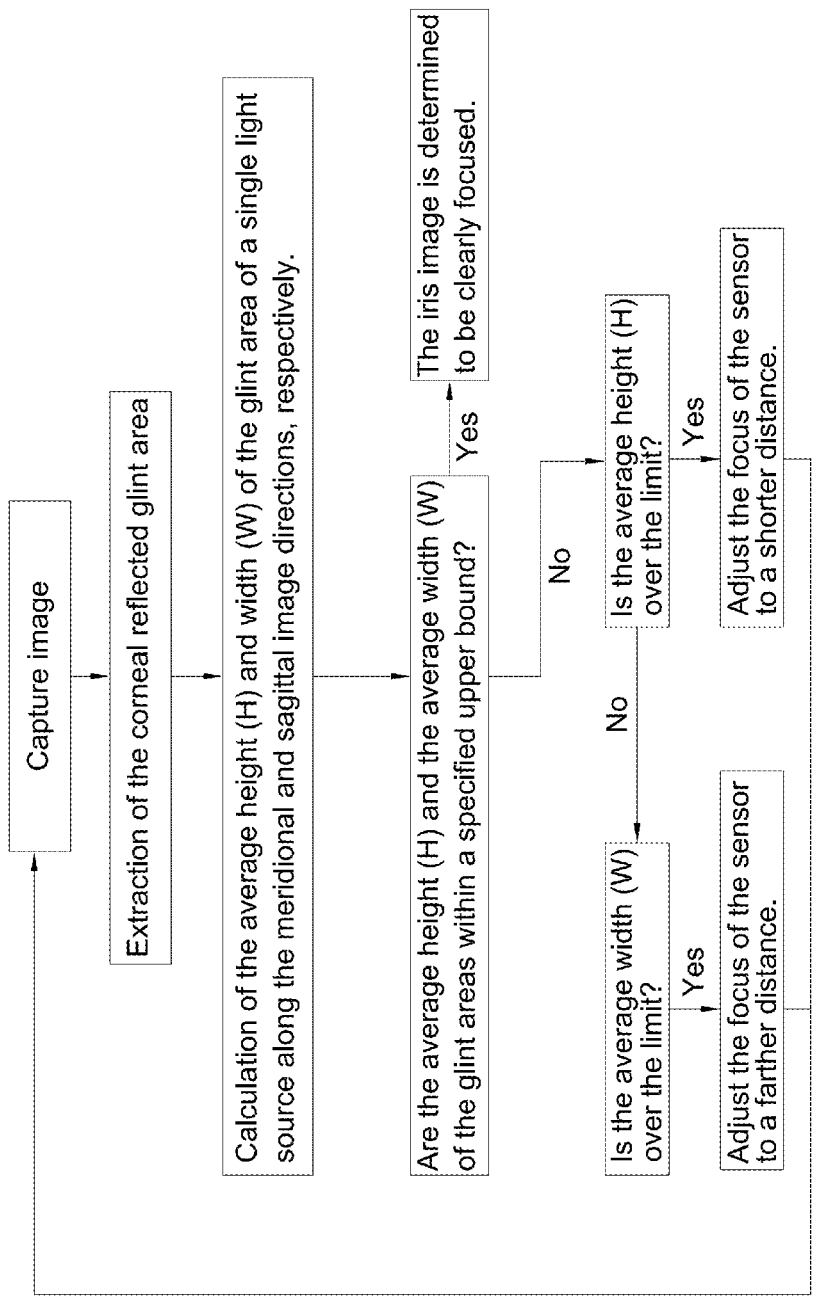
FIG. 5 is a flowchart illustrating a method of operating the iris image definition estimation system using the astigmatism of the corneal reflection of a non-coaxial light source according to an embodiment of the invention.

As presented in FIG. 5, a flowchart illustrates a method of operating the iris image definition estimation system using the astigmatism of the corneal reflection of a non-coaxial light source according to an embodiment of the invention:

(1) The non-coaxial light source 1 produces an incident light 5 which is transmitted into the cornea at an oblique angle deviating from the axis, which consequently results in astigmatism and causes the formation of the un-reciprocal meridional virtual image 6 and sagittal virtual image 7 behind the cornea. These two images will form an easily detectable glint area which is captured by the sensor 2.

(2) Extraction of the corneal reflected glint area.

(3) Calculation of the average height (H) and width (W) of the glint area of a single light source along the meridional and sagittal image directions, respectively.

(4) If the average height (H) and the average width (W) of the glint areas are within a specified upper bound, the iris image is determined to be clearly focused.

(5) If the average height (H) of the meridional glint areas is greater than the bound, then adjust the focus of the sensor 2 to a shorter distance or instruct the user to step back. On the other hand, if the average width (W) of the sagittal glint areas is greater than the bound, then adjust the focus of the sensor 2 to a farther distance or instruct the user to step forward.

Finally, repeat the procedure from step 1 to step 4 and allow auto focus to improve the resolution of the iris 3 image.

The present invention provides an iris image definition estimation system using the astigmatism of the corneal reflection of a non-coaxial light source and presents at least the following advantages.

(1) The method of calculation is easy and fast, and additional training for users to acquire the skills to adjust the focus is not necessary, which can dramatically reduce the time for focus adjustment and multiple errors resulting from guiding focus.

(2) Since the system utilizes an already-existing sensor 2 and light source of an iris 3 recognition system directly, no additional equipment is needed. Therefore, the manufacturing costs can be reduced with respect to prior art devices.

Many changes and modifications in the above described embodiments of the invention can be carried out without departing from the scope thereof. Accordingly, to promote the progress in science and the useful arts, the invention is disclosed and is intended to be limited only by the scope of the appended claims.

What is claimed is:

1. A novel iris image definition estimation system using an astigmatism of the corneal reflection of a non-coaxial light source where virtual images of a light source are measured by a sensor and used for focus adjustment, comprising:
   a non-coaxial light source which produces an incident light deviating from an optical axis which is transmitted into a cornea at an oblique angle;
   a meridional virtual image and a sagittal virtual image formed behind the cornea due to astigmatism of corneal reflection;
   a sensor which captures a composite glint area formed by the meridional and the sagittal virtual images, and subsequently, provides information to adjust a direction of focusing.

2. The iris image definition estimation system using the astigmatism of the corneal reflection of a non-coaxial light source of claim 1, wherein a size of the composite glint area is used to adjust the focus, and a height and width of the glint measured along the meridional and the sagittal image directions is used to adjust the direction of focusing.

3. The iris image definition estimation system using the astigmatism of the corneal reflection of a non-coaxial light source of claim 1, wherein a height of the glint area is measured along the meridional image direction;
  if the height of the composite glint area is over the limit, the sensor focus is adjusted to a shorter distance to give better resolution.

4. The iris image definition estimation system using the astigmatism of the corneal reflection of a non-coaxial light source of claim 1, wherein a width of the glint area is measured along the sagittal image direction;
  if the width of the composite glint area is over the limit, the sensor focus is adjusted to a farther distance to give better resolution.

5. The iris image definition estimation system using the astigmatism of the corneal reflection of a non-coaxial light source of claim 1, wherein a shape of the composite glint area formed by the meridional and the sagittal images changes accordingly as the sensor focuses at different locations.

6. The iris image definition estimation system using the astigmatism of the corneal reflection of a non-coaxial light source of claim 5, wherein a size of the glint area can be used for estimation of the focusing accuracy; and the size of the areas of the meridional and the sagittal images can provide information for adjustment of focusing direction.

7. The iris image definition estimation system using the astigmatism of the corneal reflection of a non-coaxial light source of claim 5, wherein the glint area of the meridional image after defocus is meridional glint area;
  if the size of the meridional glint area is over the limit, the sensor focus is adjusted to a shorter distance to give better resolution.

8. The iris image definition estimation system using the astigmatism of the corneal reflection of a non-coaxial light source of claim 5, wherein the glint area of the sagittal image after defocus is sagittal glint area;
  if the size of the sagittal glint area is over the limit, the sensor focus is adjusted to a farther distance to give better resolution.

* * * * *